United States Patent [19]
Mao et al.

[11] 3,946,038
[45] Mar. 23, 1976

[54] N,N'-BIS(1,1-DIOXOHYDROTHIENYL)-DIAMINOALKANES

[75] Inventors: Chung-Ling Mao, Sandy Hook, Conn.; Lynn A. Bakker, Granger, Ind.

[73] Assignee: Uniroyal, Inc., New York, N.Y.

[22] Filed: Nov. 6, 1974

[21] Appl. No.: 521,328

Related U.S. Application Data

[62] Division of Ser. No. 439,192, Feb. 4, 1974.

[52] U.S. Cl. ... 260/330.5; 260/2.5 AM; 260/75 NH; 260/77.5 AM; 260/332.1
[51] Int. Cl.² ........................................ C07D 333/66
[58] Field of Search ...................... 260/330.5, 332.1

[56] References Cited
UNITED STATES PATENTS

| | | | |
|---|---|---|---|
| 2,666,762 | 1/1954 | Cusic | 260/330.5 |
| 2,666,763 | 1/1954 | Cusic | 260/330.5 |
| 3,196,163 | 7/1965 | Argyle et al. | 260/332.1 |
| 3,887,503 | 6/1975 | Mao | 260/332.1 |

Primary Examiner—Sherman D. Winters
Attorney, Agent, or Firm—James J. Long

[57] ABSTRACT

Certain N,N'-bis(1,1-dioxohydrothienyl)diaminoalkanes, e.g., N,N'-bis(1,1-dioxotetrahydro-3-thienyl)-1,2-diaminopropane, useful as chain extenders for poly-urethanes, especially high resiliency, flexible poly-urethane foams.

24 Claims, No Drawings

N,N'-BIS(1,1-DIOXOHYDROTHIENYL)-DIAMINOALKANES

This is a division of application Ser. No. 439,192, filed Feb. 4, 1974.

This invention relates to certain new N,N'-bis-(1,1-dioxohydrothienyl) diaminoalkanes, a method of chain-extending polyurethanes therewith, and the resulting chain-extended polyurethanes.

In the manufacture of polyurethanes (long chain polyol-polyisocyanate reaction products) it is conventional to employ a "chain extender" which is ordinarily a polyfunctional organic compound having two or more reactive hydrogen atoms (reactive toward isocyanate; as determined by what is known as the Zerewitinoff method) as an aid in building up a polyurethane molecular structure having desirable properties. In practice, the requirements of a chain extender can be quite complex and exacting, and unfortunately many of the conventional ones suffer from various shortcomings in at least certain respects. One widely used chain extender is carcinogenic. To obviate this and other disadvantages there has accordingly been a continuing search by those skilled in the art for new chain extending agents.

The present invention is based on the discovery of certain new compounds, believed to be non-carcinogenic, which are surprisingly useful as chain extenders for polyurethanes. The new chemicals of the invention are N,N'-bis(1,1-dioxohydrothienyl)diaminoalkanes having the following formulas I or II:

Formula I

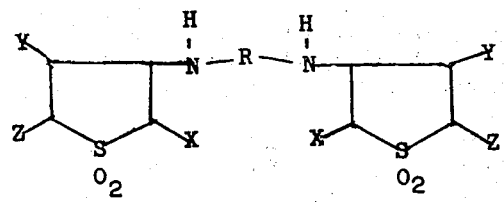

Formula II

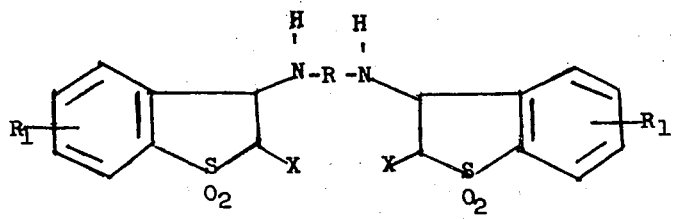

Wherein:

X and Z may be the same or different and may be hydrogen, an alkyl group having 1 to 5 carbon atoms or a halogen atom;

Y may be hydrogen, an alkyl group having 1 to 5 carbon atoms, or an alkoxy group having 1 to 5 carbon atoms;

$R_1$ may be hydrogen, an alkyl group having 1 to 5 carbon atoms, an alkoxy group having 1 to 5 carbon atoms or a halogen atom;

R may be a straight chain or branched chain alkylene group having 1 to 16 carbon atoms, a cycloalkylene group having 4 to 6 carbon atoms,

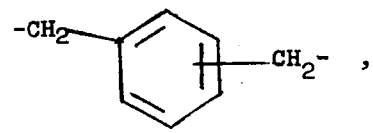

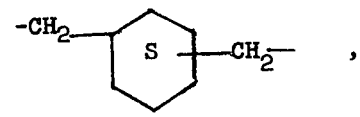

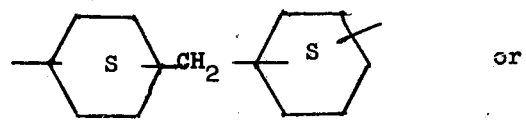

or

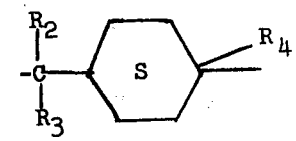

, wherein $R_2$, $R_3$ and $R_4$ may be the same or different and may be hydrogen or an alkyl group having 1 to 5 carbon atoms.

The heterocyclic diaminoalkanes of this invention are useful as chain extenders for polyurethanes and specifically for high resiliency, flexible polyurethane foams which exhibit a unique combination of physical properties such as high tensile strength, high tear resistance, high elongation, high resilient properties and low compression set. The chain extenders of the invention are also useful for making solid polyurethane elastomers and thermoplastics, for example from castable polyurethane prepolymers.

The novel compounds of this invention may be formed by a one-step synthesis starting with known thiophene 1,1-dioxides and the appropriate diamines in a suitable solvent.

The N,N'-bis(1,1-dioxotetrahydro-3-thienyl)-diaminoalkanes of Formula I are formed by reacting a 4,5-dihydrothiophene 1,1-dioxide III with the appropriate diaminoalkane IV according to the following scheme (wherein the symbols have the meanings previously assigned):

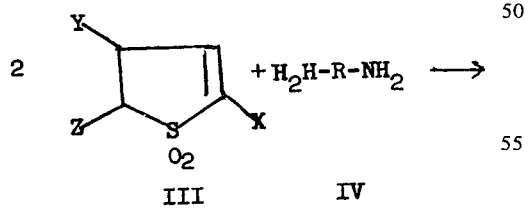

III          IV

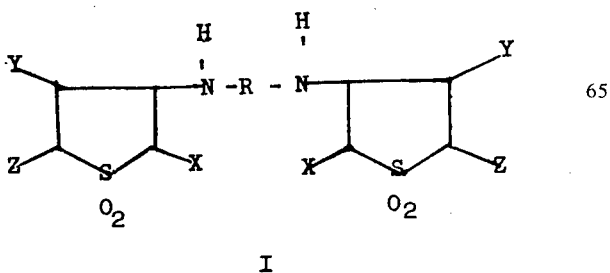

I

The N,N'-bis[3-(1,1-dioxo-2,3-dihydrobenzo[b]-thienyl)]diaminoalkanes of Formula II may be formed by reacting a benzo[b]thiophene 1,1-dioxide with the appropriate diaminoalkane VI according to the following scheme (wherein the symbols are as defined above):

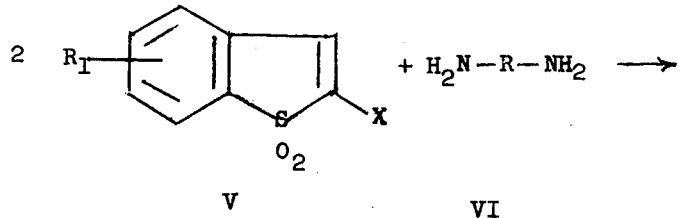

V            VI

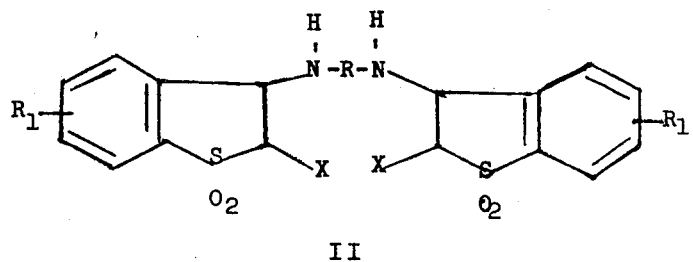

II

In general, two moles of the thiophene dioxide are reacted with one mole of the appropriate diaminoalkane. The reaction temperature is generally kept at 30°–150°C. and the reaction times will vary from two to twenty-four hours depending upon the thiophene dioxide and the diaminoalkane employed. The reaction solvents used in this reaction are water, alcohol-water mixtures and alcohols. Examples of alcohols that may be employed include methanol, ethanol, propanol, isopropanol, butanol, pentanol, hexanol and cyclohexanol.

Any of the 4,5-dihydrothiophene 1,1-dioxides having the following general formula (wherein X, Y, Z are as defined above) may be used as the starting material III for making the N,N'-bis(1,1-dioxotetrahydro-3-thienyl)diaminoalkanes I.

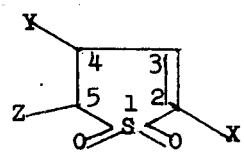

Similarly any of the benzo[b]thiophene 1,1-dioxides having the following general formula (wherein X and $R_1$ are as defined above) may be used as the starting material V for making the N,N'-bis[3-(1,1-dioxo-2,3-dihydrobenzo[b]thienyl)]diaminoalkanes II.

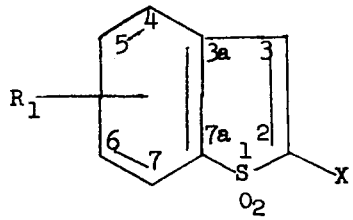

Exemplary of such thiophene dioxides are 4,5-dihydrothiophene 1,1-dioxide, 2-methyl-4,5-dihydrothiophene 1,1-dioxide, 2-chloro-4,5-dihydrothiophene 1,1-dioxide, 2-bromo-4,5-dihydrothiophene 1,1-dioxide, 2,5-dimethyl-4,5-dihydrothiophene 1,1-dioxide, 2-ethyl-4,5-dihydrothiophene 1,1-dioxide, 2-chloro-4-methyl-4,5-dihydrothiophene 1,1-dioxide, 4-phenyl-4,5-dihydrothiophene 1,1-dioxide, 2-chloro-4-phenyl-4,5-dihydrothiophene 1,1-dioxide, 2,5-dichloro-4,5-dihydrothiophene-1,1-dioxide. 2-bromo-5-phenyl-4,5-dihydrothiophene 1,1-dioxide, 4,5-5-trimethyl-4,5-dihydrothiophene 1,1-dioxide, 4-ethyl-4,5-dihydrothiophene 1,1-dioxide, 5,5-dimethyl-4,5-dihydrothiophene 1,1-dioxide, benzo[b]thiophene 1,1-dioxide, 2-chlorobenzo[b]thiophene 1,1-dioxide, 5-chlorobenzo[b]thiophene 1,1 dioxide, 5-ethylbenzo[b]thiophene 1,1-dioxide, 5-methoxybenzo[b]thiophene 1,1-dioxide, 2-chloromethyl-benzo[b]thiophene 1,1-dioxide, 2,5-dichlorobenzo[b]thiophene 1,1-dioxide, 2-ethylcarboxybenzo[b]thiophene 1,1-dioxide, 5,7-dimethylbenzo[b]thiophene 1,1-dioxide, and the like.

Any diaminoalkane having the following general formula (wherein R is as previously defined) may be used in preparing the chemicals of this invention:

$H_2N-R-NH_2$

Exemplary of such diaminoalkanes are 1,2-diaminoethane, 1,3-diaminopropane, 1,2-diaminopropane, 1,4-diaminobutane, 1,2-diamino-2-methylpropane, 1,5-diaminopentane, 1,6-diaminohexane, 1,2-diaminocyclohexane, 1,3-diaminocyclohexane, 1,4-diaminocyclohexane, 1,7-diaminoheptane, 1,8-diaminooctane, 1,10-diaminodecane, 1,12-diaminododecane, 1,8-diamino-p-menthane, alpha,alpha'-diamino-m-xylene, alpha,alpha'-diamino-p-xylene, 1,3-diaminomethylcyclohexane, 1,4-diaminomethylcyclohexane, 4,4'-methylene-bis-(aminocyclohexane), 1,6-diamino-2,2,4-trimethylhexane, and the like.

By way of non-limiting example, there may be mentioned as typical of the chain extenders of the invention such chemicals as N,N'-bis(1,1-dioxotetrahydro-2-methyl-3-thienyl)-1,4-diaminobutane, N,N'-bis(1,1-dioxotetrahydro-2-amyl-5-methyl-3-thienyl)-1,10-diaminodecane, N,N'-bis(1,1-dioxotetrahydro-3-ethyl-3-thienyl)-1,4-diaminocyclohexane, N,N'-bis(1,1-dioxotetrahydro-2,5-dichloro-4-ethyl-3-thienyl)-1,2-diaminoethane, N,N'-bis(1,1-dioxotetrahydro-4-methoxy-5-amyl-3-thienyl)-2,2,4-trimethyl-1,6-diaminohexane, N,N'-bis(1,1-dioxotetrahydro-2-bromo-4-propyl-3-thienyl)-1,16-diaminohexadecane, N,N'-bis(1,1-dioxotetrahydro-5-butyl-3-thienyl)-1,4-bis(aminomethyl)benzene, N,N'-bis(1,1-dioxotetrahydro-2,5-dichloro-4-methyl-3-thienyl)-1,2-bis-(aminomethyl)benzene, N,N'-bis(1,1-dioxotetrahydro-2-propyl-5-bromo-3-thienyl)-4,2'-methylenebis(cyclohexane), N,N'-bis(1,1dioxotetrahydro-3-thienyl)-1,8-diamino-p-methane, N,N'-bis[3-(1,1-dioxo-2,3-dihydro-2-chlorobenzo[b]thienyl)]-1,2-diaminoethane, N,N'-bis[3-(1,1-dioxo-2,3-dihydro-2-ethylcarboxy-5-chlorobenzo[b]thienyl)]-1,6-diaminohexane, N,N'-bis[3-(1,1-dioxo-2,3-dihydro-2-methyl-6-butylbenzo[b]thienyl)]-1,4-diaminocyclohexane, N,N'-bis[3-(1,1-dioxo-2,3-dihydro-4-bromobenzo[b]thienyl)]-1,8-diamino-p-methane, N,N'-bis[3-(1,1-dioxo-2,3-dihydro-2-bromo-7-ethylbenzo[b]thienyl)]-1,12-diaminododecane, N,N'-bis[3-(1,1-dioxo-2,3-dihydro-5-methoxybenzo[b]thienyl)]-2,2,5-trimethyl-1,6-diaminohexane, N,N'-bis[3-(1,1-dioxo-2,3-dihydro-2,6-dichlorobenzo[b]thienyl)]-1,2-bis(aminomethyl)benzene, and the like.

A preferred subclass of compounds of Formula I are those in which X, Y and Z are hydrogen and R is an alkylene group having 2 to 12 carbon atoms. Particularly preferred compounds of this subclass are those selected from N,N'-bis(1,1-dioxotetrahydro-3-thienyl)-1,2-diaminoethane, N,N'-bis(1,1-dioxotetrahydro-3-thienyl)-1,2-diaminopropane, N,N'-bis(1,1-dioxotetrahydro-3-thienyl)-1,3-diaminopropane, N,N'-bis(1,1-dioxotetrahydro-3-thienyl)-1,4-diaminobutane, N,N'-bis(1,1-dioxotetrahydro-3-thienyl)-1,2-diamino-2-methylpropane, N,N'-bis(1,1-dioxotetrahydro-3-thienyl)-1,6-diamino-2,2,4-trimethylhexane, N,N'-bis(1,1-dioxotetrahydro-3-thienyl)-1,6-diaminohexane, and N,N'-bis(1,1-dioxotetrahydro-3-thienyl)-1,10-diaminodecane.

Another preferred subclass of compounds of Formula I are those in which X is hydrogen or halogen, Y and Z are the same or different and are hydrogen or an alkyl group having 1 to 5 carbon atoms, and R is an alkylene group having 2 to 12 carbon atoms, a cycloalkylene group having 4 to 6 carbon atoms,

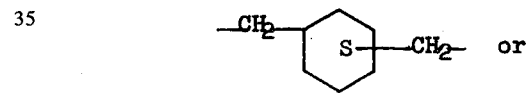

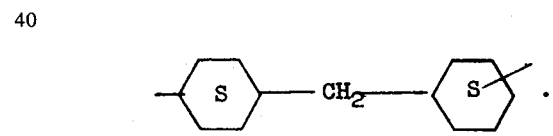

Particularly preferred compounds of this subclass are N,N'-bis(1,1-dioxotetrahydro-3-thienyl)-alpha, alpha'-diamino-m-xylene, N,N'-bis(1,1-dioxotetrahydro-3-thienyl)-1,3-bis(aminomethyl)cyclohexane, N,N'-bis(1,1-dioxotetrahydro-3-thienyl)-1,2-diaminocyclohexane, N,N'-bis(1,1-dioxo-2-chlorotetrahydro-3-thienyl)-1,2-diaminoethane, and N,N'-bis(1,1-dioxotetrahydro-3-thienyl)-4,4'-methylenebis (aminocyclohexane).

A preferred subclass of compounds of Formula II are those in which X is hydrogen, $R_1$ is hydrogen, an alkyl group having 1 to 5 carbon atoms or halogen and R is an alkylene group having 2 to 12 carbon atoms. Particularly preferred compounds of this subclass are N,N'-bis[3-(1,1-dioxo-2,3-dihydrobenzo[b]thienyl)]-1,2-diaminoethane and N,N'-bis[3-(1,1-dioxo-2,3-dihydrobenzo[b]thienyl)]-1,2-diaminopropane.

Another preferred subclass of compounds of formula II are those in which X is hydrogen or halogen, $R_1$ is hydrogen, an alkyl group having 1 to 5 carbon atoms or halogen, and R is

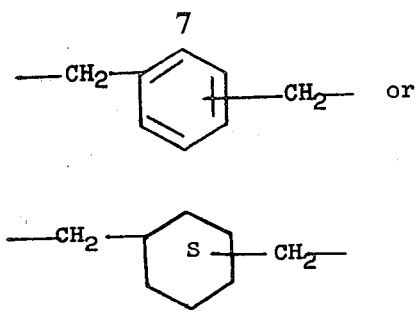

Particularly preferred chemicals of this subclass are N,N'-[3-(1,1-dioxo-2,3-dihydrobenzo[b]thienyl)]-alpha, alpha'-diamino-m-xylene and N,N'-bis[3-(1,1-dioxo-2,3-dihydrobenzo[b]thienyl)]-1,3-bis(aminomethyl)cyclohexane.

To employ the present compounds as chain extending agents for polyurethanes the compounds may simply be substituted at least in part for the conventional chain extending agents in any conventional polyurethane formulation of the kind ordinarily employing a chain extender. The proportions of the present chain extender employed may be the same as in conventional practice and the chain-extending reaction may likewise be carried out under the same conditions as are usually employed in conventional polyurethane chain extension. Polyurethane systems of the so-called one-shot type, or of the prepolymer type, may be employed, and the final product may be foam (either rigid or flexible) or a solid, whether elastomeric or otherwise, including thermoplastic polyurethanes, polyurethane surface coatings, etc. As is well understood by those skilled in the art, polyurethane forming systems conventionally involve a combination of at least one long chain polyol (whether a polyester polyol, a polyether polyol or a polyhydrocarbon polyol) and at least one organic polyisocyanate, whether a diisocyanate or a polisocyanate of higher functionality, of aliphatic, cycloaliphatic, or aromatic type. The relative proportions of polyol and polyisocyanate may be as in conventional practice appropriate to the particular kind of final product desired and the processing or fabricating method chosen.

The polyether types of polyols employed in making polyurethanes include, as is well known to those skilled in the art, poly(oxyalkylene) glycols [e.g. poly(oxyethylene) glycol, poly(oxypropylene) glycol, poly(oxytetramethylene) glycol, etc.] and higher polyether polyols, such as triols [e.g. poly(oxypropylene triol)], including polyether polyols of higher functionality than three [e.g., poly(oxypropylene adducts of pentaerythritols) and poly(oxypropylene adducts of sorbitol)]. Mention may be made of such polyether polyols as poly(oxypropylene)-poly(oxyethylene)glycol, poly(oxypropylene) adducts of trimethylol propane, poly(oxypropylene)-poly(oxyethylene)adducts of trimethylolpropane, poly(oxypropylene) adducts of 1,2,6-hexanetriol, poly(oxypropylene)-poly(oxyethylene) adducts of ethylenediamine, poly(oxypropylene) adducts of ethanolamine, and poly(oxypropylene) adducts of glycerine.

The polyester types of polyols used in making polyurethanes are likewise well known in the art and require no detailed description here. It will be understood that they include chain extended polyesters made from a glycol (e.g., ethylene and/or propylene glycol) and a saturated dicarboxylic acid (e.g., adipic acid). By way of non-limiting example there may be mentioned poly(ethylene adipate) glycol, poly(propylene adipate) glycol, poly(butylene adipate) glycol, poly(caprolactone) glycol, poly(ethylene adipate-phthalate) glycol, poly-(neopentyl sebacate) glycol, etc. Small amounts of trialcohols such as trimethylolpropane or trimethylolethane may be included in the polyester preparation. Polyester polyols with functionalities of three or more [e.g., glycerides of 12-hydroxystearic acid] are also useful. Suitable polyester polyols include those obtainable by reacting such polyols as 1,4-butanediol, hydroquinone bis(2-hydroxyethyl) ether, ethylene glycol, diethylene glycol, triethylene glycol, propylene glycol, dipropylene glycol, 2-methyl-2-ethyl-1,3-propanediol, 2-ethyl-1,3-hexanediol, 1,5-pentanediol, thiodiglycol, 1,3-propanediol, 1,3-butanediol, 2,3-butanediol, neopentyl glycol, 1,2-dimethyl-1,2-cyclopentanediol, 1,2-cyclohexanediol, 1,2-dimethyl-1,2-cyclohexanediol, glycerol, trimethylol propane, trimethylol ethane, 1,2,4-butanetriol, 1,2,6-hexanetriol, pentaerythritol, dipentaerythritol, tripentaerythritol, anhydroaneaheptitol, mannitol, sorbitol, methylglucoside, and the like, with such dicarboxylic acids as adipic acid, succinic acid, glutaric acid, azelaic acid, sebacic acid, malonic acid, maleic acid, fumaric acid, phthalic acid, isophthalic acid, terephthalic acid, tetrachlorophthalic acid, and chlorendic acid; the acid anhydrides and acid halides of these acids may also be used.

Among the polyhydrocarbyl polyols conventionally employed for making polyurethanes there may be mentioned by way of non-limiting example such materials as poly(butadiene) polyols, poly(butadiene-acrylonitrile) polyols and poly(butadiene-styrene) polyols.

The above polyols typically have a molecular weight of about 180 to 8000.

Conventional polyisocyanates used in polyurethane manufacture include, as is well known, aliphatic polyisocyanates, whether open chain, cycloaliphatic or araliphatic. Examples of aliphatic polyisocyanates conventionally employed are trimethylene diisocyanate, tetramethylene-1,4-diisocyanate, hexamethylene-1,6-diisocyanate, 1-methyl-2,4- and 1-methyl-2,6-diisocyanatocyclohexane and mixtures thereof, p-xylylene diisocyanate and m-xylylene diisocyanate (XDI) and mixtures thereof, 4,4'-diisocyanato-dicyclohexylmethane, isophorone diisocyanate, 2,2,4- and 2,4,4-trimethylhexamethylene diisocyanate, and the like.

Similarly, the aromatic polyisocyanates are suitable and include, by way of non-limiting example, such bodies as 2,4-toluene diisocyanate and 2,6-toluene diisocyanate and mixtures thereof (TDI, including crude and polymeric forms), 4,4'-diphenylmethane diisocyanate (MDI, including crude and polymeric forms), p-phenylene diisocyanate, 2,4,6-tolylene triisocyanate, 4,4'4''-triphenylmethane triisocyanate, 2,2-bis(p-isocyanato-phenyl)-propane, polymeric methylene bis(phenyl-4-isocyanate) (e.g., PAPI), naphthalene-1,5-diisocyanate, 3,3'-dimethyl-4,4'-biphenylene diisocyanate, 3,3'-dimethyoxy-4,4'-biphenylene diisocyanate, 3,3'-diphenyl-4,4''-biphenylene diisocyanate, 4,4'-biphenylene diisocyanate, 3,3'-dichloro4,4'-biphenylene diisocyanate, and the like. Mixtures of two or more such diisocyantes may also be used. Triisocyanates typically obtained by the reaction of three moles of an arylene diisocyante with one mole of triol — for example, the reaction product formed from three moles of tolylene diisocyanate and one mole of hexanetriol or of trimethylol propane, may be employed.

In one important aspect, the invention is directed to an improved flexible resilient polyurethane foam and method of making the same, employing the new chemicals described herein as chain extenders. Thus, it is well known that polyetherpolyol-polyisocyanate foams can be made by reacting a non-linear slightly branched polyether glycol or polyol, a diisocyanate, and a polyfunctional chain extender. The present invention is based in part on the discovery that polyurethane foam having a remarkable combination of desirable physical properties surprisingly results when the new N,N'-bis(1,1-dioxohydrothienyl)diaminoalkanes are employed as bifunctional chain extenders. The foams of this invention are characterized by high tensile strength, high tear resistance and low compression set. This unique combination of physical properties is largely determined by the unique chain extenders employed.

Formation of the preferred foam products of this invention may be accomplished in a one-shot system by reacting the polyol with excess polyfunctional isocyanate and the new chain extender of the invention in the presence of water and cell modifying agents, e.g. silicone such as trimethyl end-blocked dimethyl polysiloxanes. The polyfunctional isocyanate is typically present in amount of 5%–300%, say 40% by weight of the polyol. The binary chain extender of the invention is frequently present in the one-shot foam formulation in amount of 0.5 to 15 %, preferably 1 to 10%, by weight of the polyol. The water is employed in amount to react with the isocyanate to liberate sufficient gas (carbon dioxide) to produce a foam of the desired physical characteristics. From 0.6% to 10%, say 4% water (by weight of polyol) will give good results.

The mixing of the constituents in the one-shot system is typically performed at room temperature. The polyol, chain extender of the invention, catalyst, water, flame retardant and other cell-modifying agents (surface active agents) such as trimethyl end-blocked dimethyl polysiloxanes are first mixed and then the polyisocyanate is added with vigorous stirring. The gas forming reaction, the chain extension and the cross linking reactions start simultaneously when the polyisocyanate is added.

Some examples of useful catalysts are N-methyl-morpholine, N-ethyl-morpholine, triethyl amine, triethylene diamine (Dabco), N,N'-bis(2-hydroxylpropyl)-2-methyl piperazine, dimethyl ethanol amine, tertiary amino alcohols, tertiary ester amines and the like.

In addition to or in place of water the formulation may include a blowing agent of the kind conventionally employed in making polyurethane foam, usually a volatile organic liquid (e.g. boiling within the range of from 50° to 150°F) such as pentane, trichlorofluoromethane, trichloromethylene, tetrachloroethylene, trichlorotrifluoroethane, trichloroethane, methylene chloride, dibromotetrafluoroethane, carbon tetrachloride, etc.

The resulting one-shot foams of the invention surprisingly are characterized by a unique combination of physical properties such as high tensile strength, high tear resistance, high elongation, good resilience properties and low compression set. These flexible foams find utility as automobile and furniture cushioning materials, pillows, mattresses and carpet underlays.

Another important form of the invention is concerned with solid polyurethanes, particularly those made by the so-called prepolymer technique wherein the polyol is prereacted with an excess of the polyisocyanate, and thereafter the prepolymer is chain-extended or cured, using the bifunctional chain extending agent of the invention. Using liquid prepolymers cast elastomeric (or thermoplastic) aritcles and coatings having highly useful properties may be made in this way.

The following examples demonstrate the invention.

EXAMPLE I

This example illustrates the preparation of a typical N,N'-bis(1,1-dioxotetrahydro-3-thienyl) diaminoalkane of this invention, N,N'-bis(1,1-dioxotetrahydro-3-thienyl)-1,2-diaminoethane.

To a 500 ml. round bottom flask equipped with condenser, thermometer and a stirrer were introduced 118 g. (1.0 mole) of 4,5-dihydrothiophene 1,1-dioxide, 200 ml. of 70% by weight aqueous ethanol and 30 g. (0.5 mole) of 1,2-diaminoethane (ethylenediamine). The reaction mixture was heated at reflux (80°–85°C) for 4 hours. The solvent was then removed under a reduced pressure. The product, N,N'-bis(1,1-dioxotetrahydro-3-thienyl)-1,2-diaminoethane, obtained was a viscous liquid that became a solid, m.p. 60°–85°C. IR spectrum showed absorptions at 3300 cm$^{-1}$ (NH), at 1300 cm$^{-1}$ and 1140 cm$^{-1}$(SO$_2$).

Analysis for $C_{10}H_{20}N_2O_4S_2$ (percent):

| Calc'd. for | C, 40.52; | H, 6.80: | N, 9.45; | S, 21.63. |
|---|---|---|---|---|
| Found: | C, 40.05; | H, 6.85; | N, 9.10; | S, 20.96. |

EXAMPLE 2

Example I was repeated using the dioxide of Example I and substituting 1,3-diaminopropane for 1,2-diaminoethane. The resultant product, N,N'-bis(1,1-dioxotetrahydro-3-thienyl)-1,3-diaminopropane was a viscous liquid. The infrared spectrum showed absorptions at 3290 cm$^{-1}$ (NH), at 1300 cm$^{-1}$ and 1140 cm$^{-1}$ (SO$_2$).

Analysis for $C_{11}H_{22}N_2O_4S_2$ (percent).

| Cal'd for | C, 42.56; | H, 7.14; | N, 9.02; | S, 20.65. |
|---|---|---|---|---|
| Found: | C, 42.45; | H, 7.32; | N. 8.33; | S, 20.57. |

EXAMPLE 3

Example 1 was repeated using the dioxide of Example 1 and substituting 1,2-diaminopropane for 1,2-diaminoethane. The resultant product, N,N'-bis(1,1-dioxotetrahydro-3-thienyl)-1,2-diaminopropane obtained was a viscous liquid. The infrared spectrum showed absorptions at 3280 cm$^{-1}$ (NH), at 1300 cm$^{-1}$ and 1130 cm$^{-1}$ (SO$_2$). The NMR spectrum showed the bands with relative areas in agreement with the structure.

Analysis for $C_{11}H_{22}N_2O_4S_2$ (percent).

| Cal'd for | C, 42.56; | H, 7.14; | N, 9.03; | S, 20.65. |
|---|---|---|---|---|
| Found: | C, 42.27; | H, 7.26; | N, 9.03; | S, 19.98. |

EXAMPLE 4

Example 1 was repeated using the thiophene dioxide of Example 1, but substituting 1,4-diaminobutane for 1,2-diaminoethane. The product, N,N'-bis(1,1-dioxotetrahydro-3-thienyl)-1,4-diaminobutane obtained was a viscous liquid. The infrared spectrum showed absorptions at 3300 cm$^{-1}$ (NH), at 1310 cm$^{-1}$ and 1150 cm$^{-1}$ (SO$_2$).

Analysis for $C_{12}H_{24}N_2O_4S_2$ (percent).

| | | | | |
|---|---|---|---|---|
| Cal'd for | C, 44.42; | H, 7.45; | N, 8.70; | S, 19.76. |
| Found: | C, 44.59; | H, 7.59; | N, 8.61; | S, 19.27. |

EXAMPLE 5

Example 1 was repeated using the thiophene dioxide of Example 1 and substituting 1,2-diamino-2-methylpropane for 1,2-diaminoethane. The resultant product, N,N'-bis (1,1-dioxotetrahydro-3-thienyl)-1,2-diamino-2-methylpropane was obtained as a viscous liquid. The infrared spectrum and the NMR spectrum are in agreement with the structure.

Analysis for $C_{12}H_{24}N_2O_4S_2$ (percent).

| | | | | |
|---|---|---|---|---|
| Calc'd for | C, 44.42; | H, 7.45; | N, 8.70; | S, 19.76. |
| Found: | C, 44.45; | H, 7.66; | N, 9.25; | S, 19.27. |

EXAMPLE 6

Example 1 was repeated using the thiophene dioxide of Example 1 and substituting 1,6-diaminohexane for 1,2-diaminoethane. The resultant product, N,N'-bis(1,1-dioxotetrahydro-3-thienyl)-1,6-diaminohexane, obtained was a white solid, m.p. 102°–112°C (from ethanol).

The infrared spectrum showed absorptions at 3285 cm$^{-1}$ (NH), at 1310 cm$^{-1}$ and 1150 cm$^{-1}$ (SO$_2$).

Analysis for $C_{14}H_{28}N_2O_4S_2$ (percent).

| | | | | |
|---|---|---|---|---|
| Calc'd for | C, 47.70; | H, 8.00; | N, 7.94; | S, 18.17. |
| Found: | C, 47.77; | H, 7.92; | N, 7.91; | S, 18.12. |

EXAMPLE 7

Example 1 was repeated using the thiophene dioxide of Example 1 but substituting 1,2-diaminocyclohexane for 1,2-diaminoethane. The resultant product, N,N'-bis(1,1-dioxotetrahydro-3-thienyl)-1,2-diaminocyclohexane obtained was a viscous liquid that became a semi-solid. The infrared spectrum showed absorptions at 3300 cm$^{-1}$ (NH), at 1300 cm$^{-1}$ and 1130 cm$^{-1}$ (SO$_2$).

Analysis for $C_{14}H_{26}N_2O_4S_2$ (percent)

| | | | | |
|---|---|---|---|---|
| Calc'd for | C, 47.97; | H, 7.47; | N, 7.99; | S, 18.29. |
| Found: | C, 47.83; | H, 7.42; | N, 7.75; | S, 18.08. |

EXAMPLE 8

Example 1 was repeated using the thiophene dioxide of Example 1 and substituting 1,10-diaminodecane for 1,2-diaminoethane. The resultant product, N,N'-bis(1,1-dioxotetrahydro-3-thienyl)-1,10-diaminodecane obtained was a white solid, m.p. 105°–117°C. The infrared spectrum showed absorptions at 3300 cm$^{-1}$ (NH), at 1310 cm$^{-1}$ and 1120 cm$^{-1}$ (SO$_2$).

Analysis for $C_{18}H_{26}N_2O_4S_2$ (percent).

| | | | | |
|---|---|---|---|---|
| Calc'd for | C, 52.90; | H, 8.80; | N, 6.86; | S, 15.69. |
| Found: | C, 52.92; | H, 9.17; | N, 6.70; | S, 15.47. |

EXAMPLE 9

Example 1 was repeated using the thiophene dioxide of Example 1 and substituting 1,6-diamino-2,2,4-trimethyl-hexane for 1,2-diaminoethane. The resultant product, N,N'-bis(1,1-dioxotetrahydro-3-thienyl-1,6-diamino-2,2,4-trimethylhexane obtained was a viscous liquid. The infrared spectrum showed absorptions at 3290 cm$^{-1}$ (NH), at 1310 cm$^{-1}$ and 1130 cm$^{-1}$ (SO$_2$).

Analysis for $C_{17}H_{34}N_2O_4S_2$ (percent).

| | | | | |
|---|---|---|---|---|
| Calc'd for | C, 51.75; | H, 8.69; | N, 7.10; | S, 16.25. |
| Found: | C, 51.77; | H, 8.94; | N, 7.18; | S, 15.88. |

EXAMPLE 10

Example 1 was repeated using the thiophene dioxide of Example 1 but substituting alpha,alpha'-diamino-m-xylene for 1,2-diaminoethane. The resultant product, N,N'-bis(1,1-dioxotetrahydro-3-thienyl)-alpha,alpha'-diamino-m-xylene obtained was a viscous liquid. The infrared spectrum showed absorptions at 3350 cm$^{-1}$(NH) at 1300 cm$^{-1}$ and 1125 cm$^{-1}$(SO$_2$), at 780 cm$^{-1}$ and 705 cm$^{-1}$ (aromatic).

Analysis for $C_{16}H_{24}N_2O_4S_2$ (percent).

| | | | | |
|---|---|---|---|---|
| Calc'd for | C, 51.59; | H, 6.50; | N, 7.52; | S, 17.21. |
| Found: | C, 52.13; | H, 6.71; | N, 7.86; | S, 16.69. |

EXAMPLE 11

Example 1 was repeated using the diaminoalkane of Example 1 and substituting 2-chloro-4,5-dihydrothiophene 1,1-dioxide for 4,5-dihydrothiophene 1,1-dioxide. The resultant product, N,N'-bis(1,1-dioxo-2-chlorotetrahydro-3-thienyl)-1,2-diaminoethane obtained was a white solid, m.p. 142°–150°C (dec.) The infrared spectrum showed absorptions at 3300 cm$^{-1}$(NH), at 1300 cm$^{-1}$ and 1125 cm$^{-1}$ (SO$_2$).

Analysis for $C_{10}H_{18}Cl_2 N_2O_4S_2$ (percent).

| | | | | | |
|---|---|---|---|---|---|
| Calc'd for | C, 32.88; | H, 4.97; | Cl, 19.41; | N, 7.67; | S, 17.55. |
| Found: | C, 32.59; | H, 4.98; | Cl, 19.43; | N, 7.47; | S, 17.25. |

EXAMPLE 12

Example 1 was repeated using the thiophene dioxide of Example 1 and substituting 4,4'-methylene-bis-(aminocyclohexane) for 1,2-diaminoethane. The resultant product N,N'-bis(1,1-dioxotetrahydro-3-thienyl)-4,4'-methylene-bis (aminocyclohexane) obtained was a white solid, m.p. 190°–210°C (dec.). The infrared spectrum showed absorptions at 3270 cm$^{-1}$(NH), at 1310 cm$^{-1}$ and 1120 cm$^{-1}$ (SO$_2$).

Analysis for $C_{21}H_{38}N_2O_4S_2$ (percent).

| | | | |
|---|---|---|---|
| Calc'd for | C, 56.47; H, 8.50; | N, 6.27; | S, 14.33. |
| Found: | C, 56.97; H, 8.51; | N, 6.36; | S, 13.78. |

EXAMPLE 13

Example 1 was repeated using the thiophene dioxide of Example 1 and substituting 1,3-bis(aminomethyl)cyclohexane for 1,2-diaminoethane. The resultant product, N,N'-bis(1,1-dioxotetrahydro-3-thienyl)-1,3-bis-(aminomethyl)-cyclohexane, obtained was a viscous liquid. The infrared spectrum showed absorptions at 3300 cm$^{-1}$ (NH), at 1310 cm$^{-1}$ and 1110 cm$^{-1}$ (SO$_2$).

Analysis for $C_{16}H_{30}N_2O_4S_2$ (percent).

| | | | |
|---|---|---|---|
| Calc'd for | C, 50.76; H, 7.98; | N, 7.39; | S, 16.93. |
| Found: | C, 50.83; H, 8.06; | N, 7.34; | S, 16.50. |

EXAMPLE 14

This example illustrated the preparation of typical N,N'-bis [3-(1,1-dioxo-2,3-dihydrobenzo[b]thienyl)] diaminoalkane II of this invention, N,N'-bis[3(1,1-dioxo-2,3-dihydrobenzo[b]thienyl)]-1,2-diaminoethane, following the procedure of Example 1 and using 1,2-diaminoethane as the diaminoalkane and substituting benzo[b]thiophene 1,1-dioxide for 4,5-dihydrothiophene 1,1-dioxide. The reaction mixture was heated at reflux (85°C) for 20 hours and allowed to cool at room temperature. The solid product collected by filtration was dried in air, m.p. 189° – 190°C. The infrared spectrum of this product, N,N'-bis[3-(1,1-dioxo-2,3-dihydrobenzo[b]thienyl)]-1,2-diaminoethane, showed absorptions at 3300 cm$^{-1}$ (NH), at 1300 cm$^{-1}$ and 1130 cm$^{-1}$ (SO$_2$), at 790 cm$^{-1}$ and 760 cm$^{-1}$ (aromatic).

Analysis for $C_{18}H_{20}N_2O_4S_2$ (percent).

| | | | |
|---|---|---|---|
| Calc'd for | C, 55.08; H, 5.14; | N, 7.14; | S, 16.34. |
| Found: | C, 55.14; H, 5.25; | N, 7.00; | S, 16.09. |

A second isomer was isolated from the above reaction when the filtrate of the first product was cooled in ice-water. This isomer, m.p. 111°–112°C had a similar infrared spectrum to the first product. However, the two spectra were similar, but not superimposable. The spectrum of the second product also showed absorptions at 3300 cm$^{-1}$ (NH), at 1300 cm$^{-1}$ and 1130 cm$^{-1}$ (SO$_2$), at 790 cm$^{-1}$ and 760 cm$^{-1}$ (aromatic).

The NMR spectra of two isomers are vertually identical and in agreement with the structure N,N'-bis[3-(1,1-dioxo-2,3-dihydrobenzo[b]thienyl)]-1,2-diaminoethane.

Analysis for second isomer $C_{18}H_{20}N_2O_4S_2$ (percent).

| | | | |
|---|---|---|---|
| Calc'd for | C, 55.08; H, 5.14; | N, 7.14; | S, 16.34. |
| Found: | C, 54.89; H, 5.27; | N, 7.01; | S, 16.07. |

EXAMPLE 15

Example 14 was repeated using the thiophene dioxide of Example 14 but substituting 1,2-diaminopropane for 1,2-diaminoethane. The resultant product, N,N'-bis[3-(1,1-dioxo-2,3-dihydrobenzo[b]thienyl)]-1,2-diaminopropane isolated was a white solid, m.p. 163° – 167°C. (dec.) The infrared spectrum showed absorptions at 3300 cm$^{-1}$ (NH), at 1300 cm$^{-1}$ and 1125 cm$^{-1}$ (SO$_2$), at 790 cm$^{-1}$ and 760 cm$^{-1}$ (aromatic).

Analysis for $C_{19}H_{22}N_2O_4S_2$ (percent).

| | | | |
|---|---|---|---|
| Calc'd for | C, 56.13; H, 5.45; | N, 6.89; | S, 15.77. |
| Found: | C, 56.23; H, 5.58; | N, 6.94; | S, 15.70. |

EXAMPLE 16

Example 14 was repeated using the thiophene dioxide of Example 14 substituting 1,3-bis(aminomethyl)-cyclohexane for 1,2-diaminoethane. The resultant product N,N'-bis[3-(1,1-dioxo-2,3-dihydrobenzo[b]-thienyl)]-1,3-bis(aminomethyl) cyclohexane obtained was a viscous liquid that became solid (glass) at room temperature. The infrared spectrum showed absorptions at 3310 cm$^{-1}$(NH), at 1310 cm$^{-1}$ and 1100 cm$^{-1}$ (SO$_2$), at 790 cm$^{-1}$ and 760 cm$^{-1}$ (aromatic).

Analysis for $C_{24}H_{30}N_2O_4S_2$ (percent).

| | | | |
|---|---|---|---|
| Calc'd | C, 60.73; H, 6.37; | N, 5.90; | S, 13.51. |
| Found: | C, 60.76; H, 6.49; | N, 5.82; | S, 13.38. |

EXAMPLE 17

Example 14 was repeated using thiophene dioxide of Example 14 but substituting a,a'-diamino-m-xylene for 1,2-diaminoethane. The resultant product, N,N'-[3-(1,1-dioxo-2,3-dihydrobenzo[b]thienyl)]-alpha,alpha'-diamino-m-xylene obtained was a viscous liquid that became solid (glass).

Analysis for $C_{24}H_{24}N_2O_4S_2$ (percent).

| | | | |
|---|---|---|---|
| Calc'd | C, 61.51; H, 5.16; | N, 5.97; | S, 13.68. |
| Found: | C, 61.99; H, 5.28; | N, 5.88; | S, 13.32. |

EXAMPLE 18

This example illustrates that the N,N'-bis(1,1-dioxotetrahydro-3-thienyl)diaminoalkanes of this invention can also be prepared from 2,5-dihydrothiophene 1,1-dioxides and the appropriate diaminoalkanes in the presence of a base as catalyst.

To a 500 ml round-bottom flask equipped with condenser, thermometer and a stirrer were introduced 118 g. (1.0 mole) of 2,5-dihydrothiophene 1,1-dioxide, 200 ml. of 70% by weight aqueous ethanol and 37 g (0.5 mole) of 1,2-diaminopropane and 10 ml. of a 0.1 N sodium hydroxide solution. The reaction mixture was heated at 85°C for 20 hours. The solvent was then removed under a reduced pressure. The product, N,N'-bis(1,1-dioxotetrahydro-3-thienyl)-1,2-diaminopropane was obtained as a viscous liquid. The infrared spectrum of this product was superimposable with that of Example 3. This product also evaluated in high resiliency, flexible polyurethane foam (see Example 19).

As indicated above, the novel compounds of this invention find use as chain extenders in the "one-shot" system of solid foamed polyurethanes. In this system, the mixing of the constituents is typically performed at room temperatures. The polyol (polyester polyol, polyether polyol or polyhydrocarbon polyol), chain extender, catalyst, water, flame retardant and other cell-modifying agents (surface active agents), are first mixed and then the polyisocyanate is added with vigorous stirring. The gas forming reaction, the chain extension and the cross linking reactions start simultaneously when the polyisocyanate is added.

The formation of foamed products is accomplished in the one-shot system by reacting the polyol with a slight excess typically about 5 to 10 equivalent weight percent excess, of polyfunctional isocyanate in the presence of water and cell modifying agents, e.g. silicones such as trimethyl end-blocked dimethyl polysiloxanes. The polyfunctional isocyanate is typically present in amount of 5%–300%, say 40%, by weight of the polyol. The water should be present in amount to react with the isocyanate to liberate sufficient gas (carbon dioxide) to produce a foam of the desired physical characteristics. From 0.5% to 10%, say 3% water (by weight of polyol) will give good results. Some examples of useful catalysts are N-methylmorpholine, N-ethylmorpholine, triethyl amine, triethylene diamine (Dabco, trademark), N,N'-bis(2-hydroxylpropyl)-2-methyl piperazine, dimethyl ethanol amine, tertiary amino alcohols, tertiary ester amines and the like. For further details on the formulation of polyether-polyol based one shot foam formulations reference may be had to copending application Ser. No. 336,842 of Mao and Bakker, filed Feb. 28, 1973, the disclosure of which is hereby incorporated herein by reference. An example of this form of the invention is as follows:

EXAMPLE 19

This example demonstrates the use of several novel compounds of this invention as binary chain extenders in the preparation of foamed polyurethane structures using an otherwise conventional high resiliency foam formulation. For comparison purposes, the most widely used chain extender, 4,4'-methylene-bis(o-chloroaniline), which is commonly designated by the code letters MOCA was also used. The formulations and results are tabulated in Table I.

It should be noted that the polyurethane foamed structures A to F made with the novel compounds of this invention exhibit a unique combination of physical properties such as high tensile strength, high tear resistance, high elongation, high resilient properties and low compression set.

In Table I the formulations are expressed in parts by weight. The polyol is polypropyleneglycoltriol, molecular weight about 4700 made from propylene glycol (initiated with a tri-functional initiator, such as glycerol) and end-capped with, for example, 30% ethylene oxide (Voranol CP-4701; trademark). As indicated in the table the chain extenders are the compound of Example 1 (formulation A), Example 3 (formulation B,C,D), Example 5 (formulation E), and Example 18 (formulation F), as well as the conventional MOCA (formulation G). T-23P indicates a fire retardant, tris(2,3-dibromopropyl)phosphate (Firemaster T23P; trademark). The first three catalysts listed are amine types, as follows: Dabco is 1,4-diazobicyclo [2.2.2] octane; NEM is N-ethyl morpholine; A-1 is bis(2-dimethylaminoethyl) ether (NIAX A-1; trademark). The next catalyst listed, T-12 (trademark), is an organotin catalyst, dibutyl tin dilaurate. The siloxane is dimethylpoly siloxane (DC-200; trademark). TDI is toluene diisocyanate (80% 2,4-isomer, 20% 2,6-isomer, by weight). PAPI is polymeric 4,4'-methylene-diphenyl-diisocyanate. The ratio of TDI to PAPI is 90/10 in all cases. The density is expressed in pounds per cubic foot; the tensile in pounds per square inch. The units of tear are pounds per linear inch. The elongation is given in percent (at break). The set is compression set, expressed in percent. ILD indicates the indentation load deflection (that is, the load necessary to produce 25% or 65% deflection), expressed in pounds per 50 square inches. The sag is the ratio of the 65% ILD to the 25% ILD. All the properties were determined according to ASTM D-2406-68 procedures.

In each formulation in Table I the polyol, chain extender, catalyst, water, flame retardant and cell modifying agent (siloxane) are first mixed at room temperature and then the polyisocyanate is added (also at room temperature) with vigorous stirring; the liquid mixture quickly foams up and solidifies, forming a resilient polyurethane foam.

TABLE I

| MATERIAL | One-Shot Polyurethane Foam | | | | | | |
|---|---|---|---|---|---|---|---|
|  | A | B | C | D | E | F | G |
| Polyol | 100 | 100 | 100 | 100 | 100 | 100 | 100 |
| Ex. 1 | 5.0 |  |  |  |  |  |  |
| Ex. 3 |  | 5.0 | 3.0 | 1.0 |  |  |  |
| Ex. 5 |  |  |  |  | 5.0 |  |  |
| Ex. 18 |  |  |  |  |  | 5.0 |  |
| MOCA |  |  |  |  |  |  | 5.0 |
| Water | 3.5 | 3.5 | 3.5 | 3.5 | 3.5 | 3.5 | 3.5 |
| T-23 P | 3.0 | 3.0 | 3.0 | 3.0 | 3.0 | 3.0 | 3.0 |

TABLE I -continued

| MATERIAL | One-Shot Polyurethane Foam | | | | | | |
|---|---|---|---|---|---|---|---|
| | A | B | C | D | E | F | G |
| Catalysts: | | | | | | | |
| Dabco | 0.6 | 0.6 | 0.6 | 0.5 | 0.5 | 0.6 | 0.6 |
| NEM | 0.75 | 0.75 | 0.75 | 0.3 | 0.3 | 0.75 | 0.75 |
| A-1 | 0.15 | 0.15 | 0.15 | 0.15 | 0.15 | 0.15 | 0.15 |
| T-12 | — | 0.0075 | 0.0075 | — | 0.0075 | 0.0075 | 0.0075 |
| Siloxane | 1.0 | 1.0 | 1.0 | 1.0 | 1.0 | 1.0 | 1.0 |
| TDI | 39.1 | 39.4 | 39.3 | 39.1 | 39.3 | 39.4 | 39.9 |
| PAPI | 6.8 | 6.7 | 6.6 | 6.4 | 6.6 | 6.7 | 6.9 |
| Properties | | | | | | | |
| Density | 2.00 | 2.35 | 2.19 | 2.29 | 2.06 | 2.32 | 2.41 |
| Tensile | 26.0 | 20.8 | 18.07 | 17.11 | 22.46 | 22.86 | 22.03 |
| Tear | 2.57 | 2.32 | 2.05 | 2.02 | 1.99 | 2.34 | 1.87 |
| Elongation | 182 | 184 | 180 | 193 | 195 | 183 | 139 |
| Set | | | | | | | |
| 50% | — | 8.0 | 17.4 | 14.9 | 17.4 | 10.3 | 9.4 |
| 75% | — | 9.2 | 11.8 | 11.4 | 13.7 | 11.7 | 11.4 |
| ILD | | | | | | | |
| 25% | 21.5 | 21.7 | 15.6 | 19.0 | 14.5 | 22.2 | 23.2 |
| 65% | 65.5 | 66.8 | 51.9 | 59.8 | 51.8 | 66.8 | 75.2 |
| Sag | 3.04 | 3.08 | 3.33 | 3.15 | 3.57 | 3.01 | 3.26 |

EXAMPLE 20

As indicated above, the novel N,N'-bis(1,1-dioxotetrahydro-3-thienyl)diaminoalkanes also find use as binary chain extenders for castable solid polyurethanes made from polyester or polyether or polyhydrocarbon-TDI-based prepolymers. In this system the prepolymer is first prepared by reacting a predetermined excess of a diisocyanate with a polyester, polyether or polyhydrocarbon polyol such as PTMG (polytetramethylene glycol)diol and the resulting prepolymer is mixed with the binary chain extender at elevated temperatures ranging from 70°C to about 110°C as shown in Table II. The resultant reaction mixture is then poured into a mold, cured for about one hour at about 120°C and conditioned in air at 25°C and 50% relative humidity for 14 days before testing.

This procedure is employed to prepare cured polyurethanes H, I, J, K, L, M and N shown in Table II. In stocks H and I the prepolymer is a liquid urethane reaction product of hydroxy terminated polyester (e.g. ethylene glycol adipate) with a slight excess of a polyisocyanate (e.g. TDI), having an isocyanate content of approximately 3%, an amine equivalent of about 1300, a molecular weight of about 2500, specific gravity 1.2, viscosity 500 centpoises at 158°F, 1,500 centipoises at 212°F. The prepolymer used in stocks J and K is a liquid urethane reaction product of a polyether glycol (e.g. polytetramethylene ether glycol) with a slight excess of a polyisocyanate (e.g. TDI) having an isocyanate content of approximately 3%, an amine equivalent of about 1355, a viscosity of about 8 poises at 158°F and a specific gravity of 1.04. The prepolymer used in stock L, M and N was a polyether (polytetramethylene ether glycol) based liquid polymer with a slight excess of a polyisocyanate (e.g. TDI) having an isocyanate (NCO) content of 6.05 to 6.55%, an amine equivalent of about 665, and a viscosity of 6 poises at 158°F. and a specific gravity 1.07. In stock H the chain extender is the compound of Example 1; stocks I and J use the chain extender of Example 2; stock K has the chain extender of Example 3; stock L has the chain extender of Example 16; stock M has the chain extender of Example 13, and stock N the chain extender of Example 17. The amounts of prepolymer and chain extender are as shown in TAble II, expressed in parts by weight. In Table II the tensile strength is expressed in pounds per square inch. The tensile and elongation (percent elongation at break) were determined by following method ASTM D412–68 and Scott Model L Tester instructions. A jaw separtion rate of 20 in./min. and a sample thickness of 0.10 in. were used. The tear (pounds per linear inch) was obtained by following procedure of ASTM 624–54 but using a sample measuring 3 in. × 1 in. which was died out from a sheet of stock 0.10 in. thick with a 2 in. slit extending lengthwise from one end. The two legs were put in the jaws of a Scott Tester Model L and elongated until torn apart. The force required to accomplish this was recorded. The hardness (Shore A) was determined according to ASTM D2240–68. The modulus (at 100% elongation, expressed in pounds per square inch) was determined from autographic stress-strain measurements. A 0.10 in. thick sample is died out into a ring, 3 cm. inner diameter, 3.5 cm. outer diameter, placed around pullup rotating at 200 rpm and elongated at a rate of 10 inches per minute. The stress values were determined at 100% elongation.

TABLE II

| | Solid Polyurethanes | | | | | | |
|---|---|---|---|---|---|---|---|
| | H | I | J | K | L | M | N |
| Prepolymer | 145 | 145 | 145 | 145 | 125 | 125 | 125 |
| Chain Extender | 19 | 20 | 15.4 | 15.4 | 41 | 31.4 | 41.2 |
| Mixing Temperature | 70 | 70 | 70 | 70 | 80 | 110 | 110 |
| Properties | | | | | | | |
| Tensile | 4590 | 3970 | 2820 | 3155 | 3100 | 5500 | 6445 |
| Tear | 265 | 262 | 257 | 255 | 585 | 631 | 842 |
| Hardness | 63 | 62 | 76 | 75 | 91 | 93 | 94 |
| Elongation | 655 | 620 | 490 | 530 | 535 | 350 | 350 |
| Modulus | 293 | 321 | 510 | 406 | 885 | 1296 | 1844 |

We claim:
1. An N,N'-bis(1,1-dioxohydrothienyl)diaminoalkane having one of the following formulas I or II:

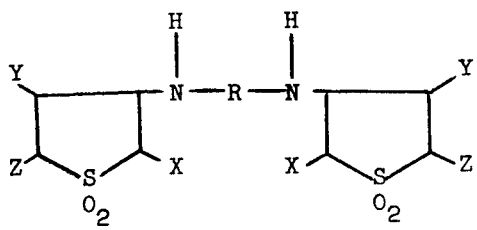

I

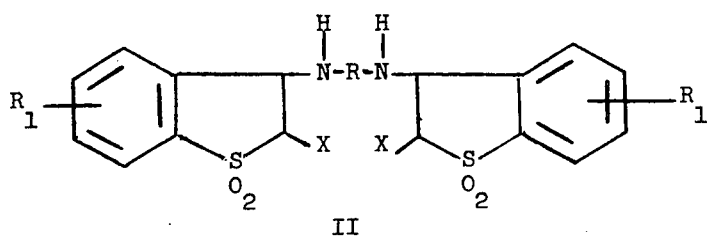

II wherein
X and Z are the same or different and are hydrogen, an alkyl group having 1 to 5 carbon atoms or halogen,
Y is hydrogen, an alkyl group having 1 to 5 carbon atoms, or an alkoxy group having 1 to 5 carbon atoms;
$R_1$ is hydrogen, an alkyl group having 1 to 5 carbon atoms, an alkoxy group having 1 to 5 carbon atoms or halogen;
R is an alkylene group having 1 to 16 carbon atoms, a cycloalkylene group having 4 to 6 carbon atoms,

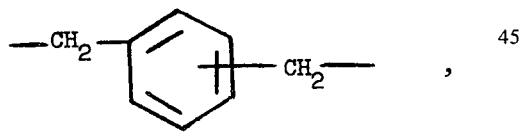,

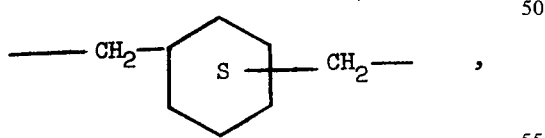,

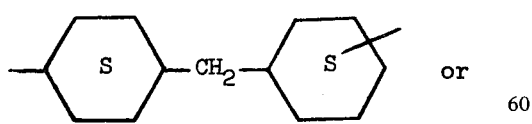 or

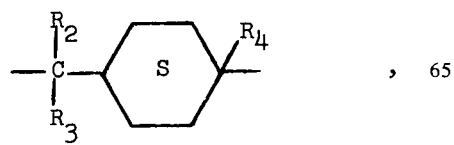, where $R_2$, $R_3$ and $R_4$ are the same or different and are hydrogen or an alkyl group having 1 to 5 carbon atoms.

2. A compound as in claim 1, which is an N,N'-bis(1,1-dioxohydrothienyl)diaminoalkane having the formula I.

3. A compound as in claim 2, in which X, Y and Z are hydrogen, and R is an alkylene group having 2 to 12 carbon atoms.

4. A compound as in claim 2 in which X is hydrogen or halogen, Y and Z are the same or different and are hydrogen or an alkyl group having 1 to 5 carbon atoms and R is an alkylene group having 2 to 12 carbon atoms, a cycloalkylene group having 4 to 6 carbon atoms,

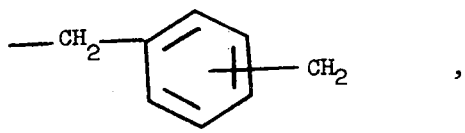,

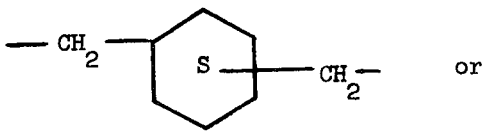 or

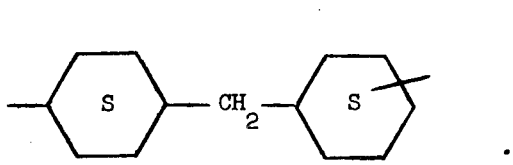,

5. A compound as in claim 1, which is an N,N'-bis(1,1-dioxohydrothienyl) diaminoalkane having the formula II.

6. A compound as in claim 5 in which X is hydrogen, R₁ is hydrogen, an alkyl group having 1 to 5 carbon atoms or halogen, and R is an alkylene group having 2 to 12 carbon atoms.

7. A compound as in claim 5 in which X is hydrogen or halogen, R₁ is hydrogen, a lower alkyl group having 1 to 5 carbon atoms or halogen, and R is

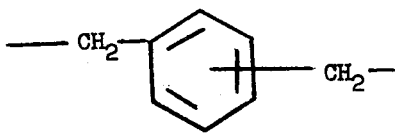 or

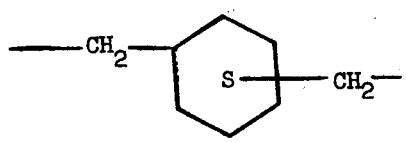

8. A compound as in claim 1 which is N,N'-bis(1,1-dioxotetrahydro-3-thienyl)-1,2-diaminoethane.

9. A compound as in claim 1 which is N,N'-bis(1,1-dioxotetrahydro-3-thienyl)-1,2-diaminopropane.

10. A compound as in claim 1 which is N,N'-bis(1,1-dioxotetrahydro-3-thienyl)-1,3-diaminopropane.

11. A compound as in claim 1 which is N,N'-bis(1,1-dioxotetrahydro-3-thienyl)-1,4-diaminobutane.

12. A compound as in claim 1 which is N,N'-bis(1,1-dioxotetrahydro-3-thienyl)-1,2-diamino-2-methylpropane.

13. A compound as in claim 1 which is N,N'-bis(1,1-dioxotetrahydro-3-thienyl)-1,6-diamino-2,2,4-trimethylhexane.

14. A compound as in claim 1 which is N,N'-bis(1,1-dioxotetrahydro-3-thienyl)-1,6-diaminohexane.

15. A compound as in claim 1 which is N,N'-bis(1,1-dioxotetrahydro-3-thienyl)-1,10-diaminodecane.

16. A compound as in claim 1 which is N,N'-bis(1,1-dioxotetrahydro-3-thienyl)-alpha,alpha'-diamino-m-xylene.

17. A compound as in claim 1 which is N,N'-bis(1,1-dioxotetrahydro-3-thienyl)-1,3-bis(aminomethyl)cyclohexane.

18. A compound as in claim 1 which is N,N'-bis-(1,1-dioxotetrahydro-3-thienyl)-1,2-diaminocyclohexane.

19. A compound as in claim 1 which is N,N'-bis(1,1-dioxo-2-chlorotetrahydro-3-thienyl)-1,2-diaminoethane.

20. A compound as in claim 1 which is N,N'-bis(1,1-dioxotetrahydro-3-thienyl)-4,4'methylene-bis-(aminocyclohexane)

21. A compound as in claim 1 which is N,N'-bis[3-(1,1-dioxo-2,3-dihydrobenzo[*b*]thienyl)]-1,2-diaminoethane.

22. A compound as in claim 1 which is N,N'-bis[3-(1,1-dioxo-2,3-dihydrobenzo[*b*]-thienyl]-1,2-diaminopropane.

23. A compound as in claim 1 which is N,N'-[3-(1,1-dioxo-2,3-dihydrobenzo[*b*]thienyl)]-alpha,alpha'-diamino-m-xylene.

24. A compound as in claim 1 which is N,N'-bis[3-(1,1-dioxo-2,3-dihydrobenzo[*b*]thienyl)]-1,3-bis-(aminomethyl)cyclohexane.

* * * * *